Figure 1:
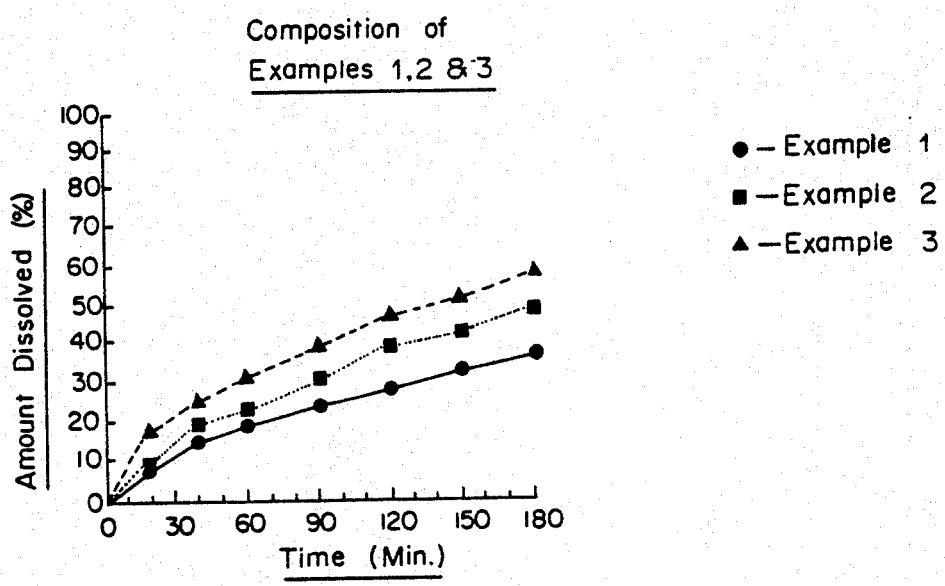

United States Patent [19]

Ushimaru et al.

[11] Patent Number: 4,702,918

[45] Date of Patent: Oct. 27, 1987

[54] PHARMACEUTICAL PREPARATIONS AND A METHOD OF MANUFACTURING THEM

[75] Inventors: Koichi Ushimaru, Kyoto; Koichi Nakamichi, Shiga; Hitoshi Saito, Kyoto, all of Japan

[73] Assignee: Nippon Shinyaku Co. Ltd., Japan

[21] Appl. No.: 762,057

[22] Filed: Aug. 2, 1985

[30] Foreign Application Priority Data

Aug. 3, 1984 [JP] Japan .................................. 59-163934

[51] Int. Cl.[4] ...................... A61K 9/22; A61K 31/715; A61K 31/20
[52] U.S. Cl. ........................................ 424/461; 514/57; 514/60; 514/560; 514/724
[58] Field of Search .................. 424/78, 80, 81, 20, 424/21, 19, 461; 514/57, 60, 560, 724, 962, 964; 424/461

[56] References Cited

U.S. PATENT DOCUMENTS

| 4,140,755 | 2/1979 | Sheth et al. | 424/21 |
| 4,540,566 | 9/1985 | Davis et al. | 424/22 |
| 4,565,890 | 3/1985 | Lain et al. | 424/21 |

Primary Examiner—J. R. Brown
Assistant Examiner—John W. Rollins, Jr.
Attorney, Agent, or Firm—Jacobs & Jacobs

[57] ABSTRACT

A sustained-release composition, which comprises (a) a substance which forms a gel in water, (b) a fat and/or oil which is solid at room temperature and (c) a pharmaceutical, said composition having a specific gravity of not more than about 1.

4 Claims, 4 Drawing Figures

Composition of Examples 1, 2 & 3

- ● — Example 1
- ■ — Example 2
- ▲ — Example 3

Composition of Example 4

PHARMACEUTICAL PREPARATIONS AND A METHOD OF MANUFACTURING THEM

The present invention relates to sustained-release compositions that remain in the digestive organs and release a pharmaceutical therefrom and a method of manufacture therefor. More particularly, it relates to sustained-release compositions that float on gastric juices or on the contents of the stomach, whereupon the pharmaceutical thereof is effectively and gradually released therefrom so that the effect of the pharmaceutical can be sustained.

Sustained-release compositions are known. Their use offers convenience to the patient by reducing the number of doses per day. Further, low concentrations of the active ingredient can be maintained so that, without losing any pharmacological effect, both toxicity and side effects can be prevented, and effective concentrations of the active ingredient can be maintained for long periods of time. Known sustained-release compositions include spansules, spantabs, repetabs, lontabs and sustained-release granules for oral preparations.

Pharmaceuticals given orally are influenced by the gastric emptying rate, which varies from person-to-person. Even in the same person it varies depending upon the nature of the contents in the stomach and its physical state and also, upon the form of preparation administered. A pharmaceutical given orally passes through the stomach within 1 to 2 hours at the earliest and within 5 to 6 hours at the latest.

This provides a reason for the lag time in absorption. cf. U. Tamassia, et al.; Bull. Chem. Farm. 117, 1978; A. H. Beckett, Yakuzaigaku 40, No. 3, 117, 1980; Ogata; Seiyaku Kojo, vols. 3, No. 93, 477, 1983; Ueno et al.; Byoiu Yakugaku, vol. 9, 53, 1983; etc. Therefore, even when the rate of release of the drug is constant, the possibility of its absorption into the blood is low and there is little reliability for use as long-acting preparations.

An absorption mechanism for active ingredients in the digestive organs has been proposed by Brodie et al. as pH partition hypothesis, which is described in, for example, Modern Pharmaceutics, pages 31-49, Marcel Pekker Inc. Since such an absorption takes place when the active ingredients are in the form of a solution, it is necessary that such ingredients are dissolved when they pass through the duodenum and the upper part of the small intestine and, therefore, it is not possible to obtain a stable and desired blood level.

In order to solve this problem, it has been proposed that the pharmaceutical preparation should remain in the stomach and that the active ingredient be made to be released therefrom gradually. In one such proposal, capsules or tablets of large diameter are used so that the selection action at the pylorus is utilized (cf. Ogata, et al.; Seiyaku Rojo, vol. 3, No. 9, 4777, 1983). This still provides large differences from person-to-person, and in addition, the residence time may vary according to the state of or contents in the stomach and, therefore, there is little reliability as a form of pharmaceutical preparation. Further, the large size of the dose makes it difficult to administer.

Other proposals include preparations using hydrophilic colloids (cf. Japan. Kokai 58/57315), hollow preparations wherein the active ingredient is coated on the outer layer (cf. Japan. Kokai 55/12411), and small bubbling capsules (cf. Japan Kokai 52/76418). Such methods, however, involve manufacturing difficulties and they are neither economical nor practical. Futhermore, the floating property of the preparations vanishes with peristaltic movement in the stomach whereupon the sustained release ability vanishes.

The present invention provides a sustained-release composition comprising (a) a substance which forms a gel in water, (b) a fat/oil which is solid at room temperature and (c) a pharmaceutical, The composition may be formed by heating the mixture at a temperature not lower than the melting point of the fat/oil, followed by cooling.

The substance (a) which forms a gel in water may be any material that forms a hydrated gel when mixed with water, such as, for example, cellulose derivatives, starch derivatives, dextrans, polysaccharides, polypeptides, proteins, acrylic acid derivatives, vinyl derivatives, and the like. More particularly, the gel-forming materials listed hereinafter may be given as representative.

1. Cellulose derivatives: carboxymethylcellulose, carboxyethylcellulose, carboxypropylcellulose, carboxymethylcellulose alkali salts, carboxyethylcellulose alkali salts, carboxypropylcellulose alkali salts, methylcellulose, hydroxypropylcellulose, hydroxypropylmethylcellulose, hydroxyethylcellulose.

2. Starch derivatives: alpha-starch, alpha-amylostarch, geletinized starch, carboxymethylstarch, carboxyethylstarch, phosphate starch, acid-treated starch, oxidized starch, dialdehyde starch, soluble starch, thin boiling starch, dextrin.

3. Dextrants: dextran, dextransulforic acid, carboxymethyldextran.

4. Polysaecharides: alginic acid, pectic acid, arabic acid, alkali salts of arabic acid, chitosan.

5. Gums: arabic gum, tragacanth, carrageenan

6. Polypeptides: polyglutamic acid, polyaspartic acid, polylysinc, polyalginine.

7. Proteins: gelatin, collagen, cesein, albumin, globulin, gluten.

8. Acrylic acid derivatives: polyacrylic acid, polymethacrylic acid, alkali salts of polymethacrylic acid, polyacrylic acid-methacrylic acid copolymer.

9. Vinyl derivatives: polyvinylpyrrolidone, polyvinyl alcohol.

The fat/oil (b) which is solid at room temperature may be, for example, higher fatty acids, high fatty acid ester derivatives, higher alcohols, higher alcohol ester derivatives, and the like. More particularly, the following fats and oils are listed as representative.

1. Higher fatty acids: lauric acid, tridecanoic acid, myristic acid, pentadecanoic acid, palmitic acid, margaric acid, stearic acid, nodecanoic acid, arachic acid, behenic acid, lignoceric acid, cerotic acid, montanic acid, etc.

2. Higher fatty acid ester derivatives: esters of the above given under item 1. with glycerol, ethyleneglycol, propyleneglycol, sorbitol, polyethyleneglycol, etc.; glycerides of saturated fatty acids obtained from animals and plants and a mixture thereof as well as hardened fat/oil of glycerides derived from such animals and plants; glycerides of unsaturated fatty acids such as oleic acid, linolic acid, linoleic acid, ricinolic acid, etc. and a mixture thereof.

3. Higher alcohols: pentadecanol, hexadecanol (cetyl alcohol), heptadecanol (stearyl alcohol), nonadecanol, eicosanol, wool alcohol, cholesterol, etc.

4. Higher alcohol esters: cholesteryl palmitate, palmitates of plant sterols, etc.

Useful fats and/or oils (b) include low melting materials, such as oleic acid monoglycerine ester (mp=35° C.), cacao butter (mp:32°-35° C.), wool fat (mp=30°-40° C.) and the like, since fats/oils that are solid at temperatures of about 40° C. or less are for the purpose of this invention "solid at room temperature." Further, individual fats/oils of a mixture (b) of fats/oils may have a melting point above 40° C., as long as the mixture (b) is "solid at room temperature".

Any pharmaceutical may be used in the present invention as long as when said pharmaceutical is mixed with a mixture of (a) a substance which forms a gel in water and (b) a fat/oil which is solid at room temperature, and heated above the melting point of the fat/oil and cooled, the specific gravity of the resulting product will not be more than substantially 1.0.

For instance, 1.8 g of barium sulfate (specific gravity: 4.5), 0.9 g of stearic acid and 0.9 g of hydroxypropylcellulose, H type (HPC-H) are mixed in a mortar, each 360 mg of the mixture is filled in capsule, the capsules are heated at 75° C. for 10 minutes and cooled to give preparations which float on the 1st and 2nd test fluids described on page 727 of "The Pharmacopoeia Of Japan," Society of Japanese Pharmacopoeia, 1982. A mixture of 1.4 g of synthetic aluminum silicate, 0.7 g of stearic acid and 0.7 g of HPC-H is kneaded in a mortar, each 280 mg of it is filled in a capsule (No. 2), and the capsules are treated as same as above. The treated capsules float on the above 1st fluid. When this is subjected to a dissolution test in accordance with the Dissolution Test described in "The Pharmacopoeia Of Japan", pages 725-733 (rotary basket method), the synthetic aluminum silicate is released for more than six hours.

Accordingly, any inorganic drug, organic drug, natural product, physiologically active substance and the like having the specific gravity of not more than that of barium sulfate can be substantially used as the pharmaceutical (c) that constitutes the active ingredient of the composition of the present invention.

Representative examples of pharmaceuticals useful in the present invention include:

1. Anti-inflammatory agents: Indomethacin, aspirin, diclofenac sodium, ketoprofen, ibuprofen, metenamic acid, dexamethasone, sodium dexamethasonesulfate, hydrocortisone, prednisolone, azulene, etc.
2. Antiulcerative agents; sulpiride, cetraxate hydrochloride, gefarnate, etc.
3. Coronary dilators: nifedipine, isosorbic dinitrate, nitroglycerine, dilthiazem hydrochloride, trapidil, dipyridamol, dilazep, etc.
4. Peripheral vasodilators: ifenprodil tartrate, cinepazet maleate, cyclaudelate, cinnarizine, pentoxyphylline, etc
5. Antibiotics: acpicillin, amoxycillin, caphalexin, crythromycin ethylsuccinate, bacampicillin hydrochloride, minocycline hydrochloride, etc.
6. Urinary antiseptics: pipemidic acid, nalidixie acid, etc.
7. Antipyretics and sedatives: aspirin, phenacetin, isopropylantipyrine, acetaminophene, benzydamine, etc.
8. Antispasmodics: propantheline bromide, atropine sulfate, oxopium bromide, timepidium bromide, butylscopolamine bromide, etc.
9. Antitussives and antiasthmatics: theophylline, aminophylline, methylephedrine hydrochloride, procatechol hydrochloride, trimethoquinol hydrochloride, codrine phosphate, sodium cromoglycate, tranilast, clofedanol, dextromethorphan hydrobromide, etc.
10. Diuretics: furosemide, acetazolamide, etc.
11. Muscle relaxants: chlophenesin carbamate, tolperisone hydrochloride, eperisone hydrochloride, etc.
12. Cerebral metaholie agents: calcium hopantenate, meclofenoxate hydrochloride, etc.
13. Minor tranquilizers: oxazolam, diazepam, cloriazepam, medazepam, tomazepam, fludiazepam, etc.
14. Major-tranquilizers: sulpiride, clocapramine hydrochloride, zotepine, etc.
15. Beta-blocking agents: pindolol, propranolol hydorchloride, carteolol hydrochloride, metoprolol tarrrate, labetalol hydrochloride, etc.
16. Antiarrhythmic agents: procainamide hydrochloride, disopyramide, ajimaline, qunidine sulfate, etc.
17. Anti-gout agents: allopurinol, etc.
18. Anticoagulants: ticlopidine hydrochloride, etc.
19. Antiepileptics: phenyloin, sodium valproate, etc.
20. Antihistaminics: chlorpheniramine malate, elemastine fumarate, mequitazine, alimemazine tartrate, cyproheptadine hydrochloride, etc.
21. Antiemetics, Antivertigo agents: diphenidol hydrochloride, methochlopromide, domperidone, betahistine mesylate, etc.
22. Mepotensive agents: dimethylaminoethyl-reserpilinate dihydrochloride, rescrinnamine, methyldopa, prazosin hydrochloride, clonidine hydrochloride, budralazine, etc.
23. Sympathomimetic agents: dihydrocrgotamine mesylate, isoproterenol hydrochloride, etilefrine hydrochloride, etc.
24. Expectorants: bromohexine hydrochloride, corbocisteine, L-ethylcysteine hydrochloride, L-methylcysteine hydrochloride, etc.
25. Oral antidiabetic agents: glibenclamide, tolbutamide, gliymidine sodium, etc.
26. Cardiovascular agents: ubidecarenone, adenosine triphosphate disodium, etc
27. Iron preparations: ferrous sulfate, anhydrous ferrous sulfate, etc.
28. Vitamins: vitamin $B_1$, vitamin $B_2$, vitamin $B_6$, vitamin $B_{12}$, vitamin C, folic acid, etc.
29. Others: flavoxate hydrochloride.

Each of the components (a), (b) and (c) may be present as a single material or a mixture of two or more thereof. The proportions of (a), (b) and (c) may be widely varied but generally it is presently preferred that component (c) will be from about 0.01 to about 85%, by weight based on the total weight of the composition. In addition, other additives may be present, such as exipients, lubricants, coloring agents and pharmaceutically acceptable carriers of diluents used in conventional pharmaceutical compositions. Generally, (c) will be combined with a mixture of from about 10 to about 90% of (a) and from 90 to about 10% of (b), by weight based on the weight of (a) and (b). Usefully, the mixture of (a) and (b) will be at least 10% by weight based on the total weight of the composition.

When the pharmaceutical (c) used in the present invention is oleophilic, it may be previously dissolved in (b) fat/oil which is solid at room temperature, then pulverized, mixed with (a) a substance which forms a gel in water, and then heated and cooled as described above. It is also possible, in the present invention, that all of (a) a substance which forms a gel in water, (b) fat/oil which is solid at room temperature and (c) pharmaceutical are mixed, the mixture is made into tablets or filled in capsules, and then they are heated and cooled.

Figure 2:
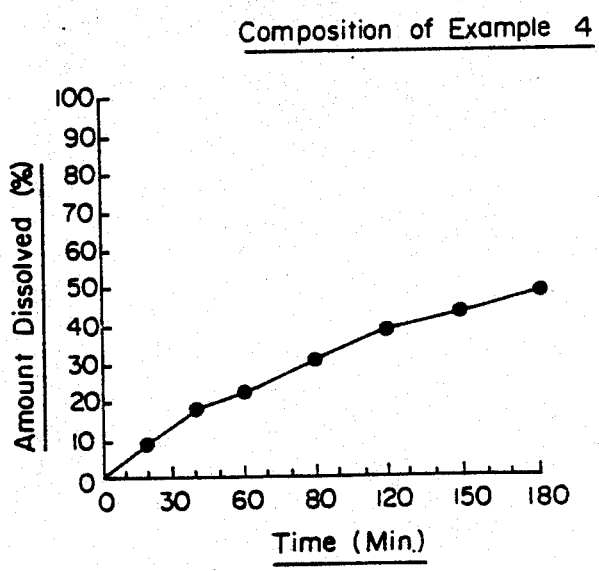
Figure 3:
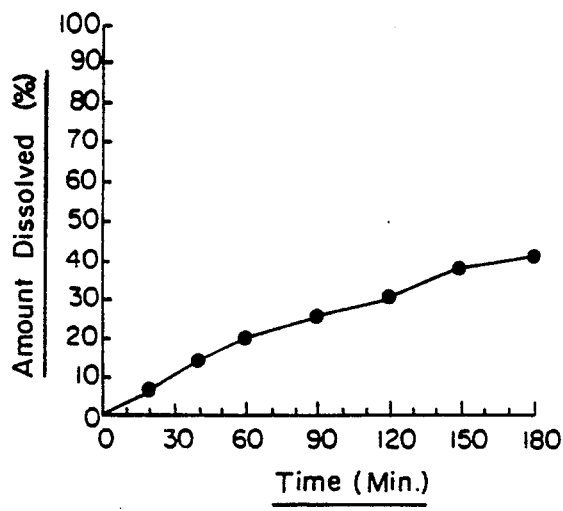
Figure 4:
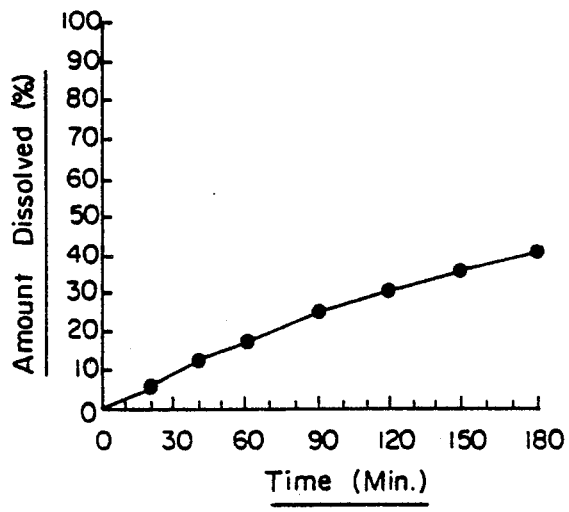

The present invention is illustrated by the accompanying drawings, in which FIGS. 1 to 4 show the sustained-release effect obtained with the sustained release compositions of the present invention. The data for FIGS. 1 to 4 were obtained using the procedure described in Test 4 described hereinafter. The pharmaceuticals used in FIGS. 1 to 4 were diphenidol hydrochloride, theophylline, cephalexin and aspirin, respectively.

As already described, the present invention comprises (a) a substance which forms a gel in water, (b) a fat/oil which is solid at room temperature, and (c) a pharmaceutical. In the resulting sustained-release compositions, the space between (a) and (c) is maintained by melting (b) followed by solidifying it. This provides a specific gravity for the sustained-release composition of the present invention of not more than substantially 1.0. It is known that the specific gravity of digestive fluids, especially that of gastric juices, is from 1.004 to 1.101 and, accordingly, the sustained-release composition of the present invention will float on digestive fluids, particularly gastric juices.

When the sustained-release compositions according to the present invention are contacted with an aqueous medium (such as gastric juice, artificial gastric juice, etc.) a hydrated gel layer is formed at the boundary surface of said medium and said sustained-release composition, whereby the pharmaceutical (c) is gradually released and, at the same time, inversion of the liquid into the sustained-release composition is prevented so that the composition floats for a long time.

As already described, when peristaltic movement takes place in the stomach, pharmaceutical preparations with weak strength are destroyed and their function as a sustained-release preparation is deteriorated. However, in accordance with the present invention, such a disadvantage does not take place. When the sustained-release compositions of the present invention are subjected to a disintegration test by placing thereof discs in a tester in accordance with The Pharmacopocia Of Japan, they do not disintegrate even for more than six hours and, in addition, it is confirmed that, during this period, the pharmaceutical (c) is constantly released.

This function of the present invention does not occur when, for example, a mixture of (a) a substance which forms gel in water and (b) fat/oil which is solid at room temperature or a mixture of (b) fat/oil which is solid at room temperature and (c) pharmaceutical; is heated at a temperature higher than the melting point of (b) followed by cooling and solidifying. Furthermore, it is observed that the preparation obtained by mere mixing of (a), (b) and (c) without the succeeding melting and cooling steps does not exihibit such a function.

The present invention has the following technical effects.

1. Sustained-release compositions of the present invention float in aqueous media and, therefore, they maintain their flotation in the stomach.
2. Sustained-release compositions of the present invention exhibit good strength and, therefore, they do not disintegrate by peristalitic movement.
3. Sustained-release compositions of the present invention exhibit reproducibility of releasing rate into aqueous media and, therefore, they can maintain the release of a constant amount of pharmaceutical (c) during the floating stage in the stomach.

Since the present invention can be conducted by the combined use of conventional techniques, the production cost of the sustained-release compositions of the present invention is low and it can be produced by simple means.

The present invention is illustrated by the following examples.

EXAMPLE 1

Diphenidol hydrochloride (5 g), 8.5 g of hydroxypropylcellulose H type, and 8.5 g of stearic acid were placed in a mortar, mixed uniformly, and aliquots of 220 mg were filled into capsules of size No. 2. The capsules were heated for 10 minutes in an electric heater at 80° C., removed, and cooled to room temperature. Sustained-release capsules, each containing 50 mg diphenidol hydrochloride, were obtained.

EXAMPLE 2

Diphenidol hydrochloride (5 g), 8.5 g of alpha-amylopectin, and 8.5 g of stearyl alcohol were used and, by treating as same as in Example 1, filled in capsules (each capsule was made filled with 220 mg of the mixture). They were heated in an electric heater set at 65° C. for 10 minutes, taken out, and cooled to room temperature to give capsules each containing 50 mg of diphenidol hydrochloride.

EXAMPLE 3

Diphenidol hydrochloride (50 g), 85 g of methylcellulose (Metolose SM-25, manufactured by Shin-etsu Kagaku KK) and 85 g of stearic acid were placed in a fluidized bed granulator-drier (manufactured by Strea-Fuji Sangyo KK) and, while fluidized at room temperature, 1500 ml of ethanol solution (Japanese Pharmacopein) was sprayed thereon to prepare granules. Each 220 mg of the resulting granules were filed in capsules (No. 2) using a capsulating machine (No. 8; Nippon Elanco KK), the resulting capsules were placed in the above fluidized bed granulator-drier, fluidized therein for 10 minutes by adjusting the inlet air temperature at 75° C., then heater was oft, cooled by supplying air of room temperature therein, and diphenidol hydrochloride capsules (each containing 50 mg) were obtained.

EXAMPLE 4

Theophylline (200 g), 120 g of alphatized potato starch and 90 g of stearic acid were taken in a fluidized bed granulator-drier as described in Example 3 and granulated by spraying with 300 ml of pure water under fluidizing at room temperature. Each 410 mg of the mixture was filled in a capsule No. 0 using a capsule filling machine. The capsules were placed in the fluidized bed granulator-drier the same as above, fluidized for 10 minutes setting the intake air temperature at 75° C., then heater was made off, and cooled with an introduction of room temperature air to give capsules each containing 200 mg of theophylline.

EXAMPLE 5

Chlorpheniramine maleate (6 g), 129 g of carboxymethylecellulose (Cellogen F-SA; manufactured by Daiichi Kogyo Seiyaku KK) and 15 g of hardened castor oil were granulated using 300 ml of 50% aqueceous ethanol by the similar way as Example 3. Each 150 mg of the mixture was filled in a capsule No. 3. The capsules were heated in an electric heater adjusted at 100 C. for 10 minutes, taken out and cooled to room temperature to give capsules each containing 6 mg of chlorpheniramine maleate.

EXAMPLE 6

Cephalexin (250 g), 100 g of hydroxypropylcellulose-H and 70 g of stearic acid were granulated by the similar way as in Example 3. Each 420 mg of the granules was filled in a capsule No. 0. The capsules were again placed in a fluidized bed granulator-drier and treated by the similar way as in Example 3 to give capsules each containing 250 mg of cephalexin.

EXAMPLE 7

Isosorlide dinitrate (20 g), 100 g of hydroxypropylcellulose-H and 80 g of ethyl alcohol were mixed. Each 200 mg of the mixture was filled in a capsule No. 2. The capsules were subjected to fluidization with heating (intake air temperature: 65° C.) for 10 minutes, the heater was turned off, and then the capsules were cooled with room temperature air to give capsules each containing 20 mg of isosorbide dinitrate.

EXAMPLE 8

Nitedipine (20 g), 100 g of hydroxypropylmethylcellulose, and 50 g of palmitic acid were granulated by the same operation as in Example 3. Each 170 mg of them was filled in a capsule No. 3. The capsules were placed in a fluidized bed granulator-drier, subjected to fluidization with heating (intake air temperature: 70° C.) for 10 minutes, the heater was turned off and the capsules were cooled with room temperature air to give each capsule 20 mg of nifedipine.

EXAMPLE 9

Diclofenar sodium (50 g), 125 g of hydroxypropylcellulose and 125 g of stearic acid were granulated by the same way as in Example 4. Each 300 mg of the granules was filled in a capsule No. 1. The capsules were placed in a fluidized bed granulator-drier, subjected to a fluidization with heated with air of intake temperature 80° C. for 10 minutes, the heater was off and cooled with air of the room temperature to give capsules each containing 50 mg of diclofenac sodium.

EXAMPLE 10

Pindolol (10 g), 70 g. methylcellulose (Metolose-SM 4000; manufactured by Shin-etsu Kagaku KK), and 60 g of cetyl alcohol were placed in a polyethylene bag, mixed well, each 140 mg of the mixture was filled in a capsule No. 3, then the capsules were placed in a fluidized bed granulator-drier, subjected to a fluidization by heating with air of intake temperature 70° C. for 15 minutes, the heater was turned off and allowed to cool with air at the temperature of the room to give capsules each containing 10 mg of pindolol.

EXAMPLE 11

Aspirin (300 g), 80 g of hydroxypropylcellulose-H and 40 g of stearic acid were subjected to granulation by the same way as in Example 3. Each 420 mg of it was filled in a capsule No. 0. The capsules were placed in a fluidized bed granulator-drier, subjected to fluidization by heating with hot air (intake temperature: 80° C.) for 15 minutes, the heater was turned off and allowed to cool with air of the room temperature to give capsules each containing 300 mg of aspirin.

EXAMPLE 12

Sodium azulenesulfonate (12 g), 186 g of hydroxypropylcellulose-M and 282 g of stearic acid were granulated by the same way as in Example 5. Each 160 mg of it was filled in a capsule No. 3. The capsules were placed in a fluidized bed granulator-drier, fluidized by heating with air (intake temperature: 80° C.) for 15 minutes, the heater was turned off and allowed to cool with air of the room temperature to give capsules each containing 4 mg of azulenesulfonic acid.

EXAMPLE 13

Ifenprodil tartrate (80 g), 180 g of hydroxypropylmethylcellulose (Metolone 90SH; manufactured by Shin-etsu Kagaku KK), and 180 g of cetyl alcohol were granulated by the same way as in Example 4. Each 220 mg of it was filled in a capsule No. 2. The capsules were then placed in a fluidized bed granulator-drier, fluidized with heating with air (intake temperature: 65° C.) for 10 minutes, the heater was then turned off, and allowed to stand with air of the room temperature to give capsules each containing 40 mg of infeuprodil tartrate.

EXAMPLE 14

Sulpiride (100 g), 130 g of hydroxypropylcellulose-H and 70 g of deodored and bleached bees wax were granulated by the same way as in Example 3. Each 300 mg of it was filled in a capsule No. 1. The capsules were placed in a fluidized bed granulator-drier, subjected to fluidization by heating with air (intake temperature: 75° C.) for 15 minutes, then the heater was turned off and allowed to cool with air of the room temperature to give capsules each containing 100 mg of sulpiride.

EXAMPLE 15

Dried aluminum hydroxide gel (300 g), 60 g of hydroxypropylcellulose-H and 90 g of hardened castor oil were granulated by the same way as in Example 3. Each 450 mg of it was filled in a capsule No. 0. The capsules were placed in a fluidized bed granulator-drier, subjected to fluidization by hot air (intake temperature 100° C.) for 15 minutes, then the heater was turned off, and allowed to cool with air of the room temperature to give capsules each containing 300 mg of dried aluminum hydroxide gel.

EXAMPLE 16

Riboflavine butyrate (60 g), 150 g of alpha-amylopectin and 300 g of stearic acid were granulated by the same way as in Example 5. Each 170 mg of it was filled in a capsule No. 3. The capsules were placed in a fluidized bed granulator-drier, subjected to fluidization by heating with hot air (intake temperature: 80° C.) for 15 minutes, then the heater was turned off, and allowed to cool with air of the room temperature to give capsules each containing 20 mg of riboflavine butyrate.

The excellent characteristics of the pharmaceutical preparation in accordance with the present invention can be confirmed by the following tests. In the tests, Valrclease (Registered Trademark) (Roche) which is a diazepam preparation and sold in West Germany as floating capsules is used as a control.

Test 1. Measurement of Flotage

A microload transformer (UT-100GR: manufactured by Shinkoh-Minevea KK) was modified to include an attachment to which the test capsules could be fixed. The force in milligrams required to sink the test capsules in water was measured electrically and reported in Table 1 below under zero shaking time.

Test 2. Measurement of Resistance Against Shaking and of Flotage

Into a separatory funnel (200 ml) was placed 100 ml of the 1st test fluid described in the Pharmacopeia of Japan. Each test sample was put thereinto and then shaken for six hours with a KH shaker (Model V.S.; amplitude: 5 cm; 300 shakings per minute). The shape was observed and the flotage was measured as in Test 1 each hour. The results are reported in Table 1 below.

TABLE 1

| Shaking Time | Example 1 Shape | Example 1 Flotage | Example 2 Shape | Example 2 Flotage | Example 3 Shape | Example 3 Flotage | Control Shape | Control Flotage |
|---|---|---|---|---|---|---|---|---|
| 0 hr | same as original | 180 | same as original | 116 | same as original | • | same as original | 178 |
| 1 | same as original | 157 | same as original | 145 | same as original | 145 | disintegrated | 0 |
| 2 | same as original | 133 | same as original | 124 | same as original | 131 | — | — |
| 4 | same as original | 118 | same as original | 103 | same as original | 115 | — | — |
| 5 | same as original | 97 | same as original | 84 | same as original | 96 | — | — |
| 6 | same as original | 86 | same as original | 73 | same as original | 85 | — | — |

Control: Valrelease capsules
Unit of the shaking time is hour; "original" means the shape of the capsule; unit of flotage is mg.

As shown in Table 1, sustained-release compositions of the present invention exhibited flotage of about 160–180 mg in the cases of Examples 1 to 3 and showed resistance against shaking and, even after six hours, the original shape of capsules was maintained. In contrast, the control preparation showed complete disintegration after shaking for only one hour. It is therefore quite apparent that the sustained-release compositions of the present invention have a strong resistance against shaking and stirring and are resistant to the peristaltic movement in the stomach.

Test 3. Disintegration Test

In accordance with the disintegration test described in pages 725 et seq. of The Pharmacopeia of Japan, a disc is placed in a tube and the disintegration of each sample was tested. The result was that, through the control capsules (Valrelease capsules) disintegrated within only 10 minutes, the sustained-release compositions of Examples 1–4 of the present invention did not disintegrate even after 240 minutes. This confirms the result of test 2.

Test 4. Dissolution Test

In accordance with the dissolution test as described in pages 725–733 of The Pharmacopoeia of Japan, a sample was sunk using a sinker in the 1st test fluid, stirred at 100 rpm, and the amount dissolved for each ingredient was measured at predetermined time intervals. Among the samples used, cephalexin, aspirin and theophylline were determined by measuring the extinctions at 260, 229 and 280 nm, respectively. As to diphenidol hydrochloride, samples were done at certain time intervals and measured by a high speed liquid chromatography. The results are given in FIGS. 1 to 4.

From the test data discussed above, it is apparent that the substained-release compositions of the present invention float on gastric juices when administered orally, and exhibit sufficient resistance against stirring and peristaltic movement in the stomach so that they are not disintegrated but rather they release the pharmaceutical in the stomach gradually.

The 1st and 2nd test fluids referred to herein are described in page 727 of The Pharmacopoeia of Japan, Tenth Edition, and are prepared as follows:

1st fluid—Dissolve 2.0 g of sodium chloride in 24.0 ml. of dilute hydrochloric acid and add sufficient water to make 1000 ml. This solution is colorless and clear, and its pH is about 1.2.

2nd fluid—To 250 ml of 0.2M monobasic potassium phosphate TS add 118 ml. of 0.2N sodium hydroxide TS and sufficient water to make 1000 ml. This solution is colorless and clear, and its pH is about 6.8.

We claim:

1. A sustained-release composition in capsule form having a specific gravity of not more than about 1, said capsules containing a mixture of (a) from about 10 to about 90% by weight of a cellulose derivative or a starch derivative which forms a gel in water and (b) from about 90 to 10% by weight of a higher fatty acid glyceride or higher alcohol or a mixture thereof which is solid at room temperature, both based on the weight of (a) and (b), and (c) from 0.01 to about 85% by weight based on the weight of (a), (b) and (c) of a pharmaceutical, said capsules having been prepared by filling capsules with said mixture of (a), (b) and (c), heating said capsules to a temperature above the melting point of (b) and cooling and solidifying said mixture.

2. The composition of claim 1, wherein (a) is hydroxypropylcllulose, methylcellose, carboxymethylcellulose, hydroxypropylmethylcellulose or alpha-starch or a mixture thereof.

3. The composition of claim 1, wherein (b) is stearic acid, palmitic acid, hardened castor oil, beeswax, stearyl alcohol or ethyl alcohol or a mixture of two or more thereof.

4. A method of making the sustained-release composition according to claim 1, in capsule form, wherein a mixture of (a), (b) and (c) is formed and filled into capsules, the capsules are heated to a temperature above the melting point of (b), whereafter the mixture is cooled and solidified.

* * * * *